(12) United States Patent
Matthias et al.

(10) Patent No.: US 9,734,420 B2
(45) Date of Patent: *Aug. 15, 2017

(54) DEVICE AND METHOD FOR INSPECTING A VOLUME OF A SAMPLE

(71) Applicants: Torsten Matthias, Wendelsheim (DE); Hans-Peter Schimon, Heiningen (DE); Jens Blecken, Fuerfeld (DE); Markus Wulf, Alzey (DE)

(72) Inventors: Torsten Matthias, Wendelsheim (DE); Hans-Peter Schimon, Heiningen (DE); Jens Blecken, Fuerfeld (DE); Markus Wulf, Alzey (DE)

(73) Assignee: Torsten Matthias, Wendelsheim (DE)

( * ) Notice: Subject to any disclaimer, the term of this patent is extended or adjusted under 35 U.S.C. 154(b) by 269 days.

This patent is subject to a terminal disclaimer.

(21) Appl. No.: 14/354,782

(22) PCT Filed: Oct. 29, 2012

(86) PCT No.: PCT/EP2012/004524
§ 371 (c)(1),
(2) Date: Apr. 28, 2014

(87) PCT Pub. No.: WO2013/060480
PCT Pub. Date: May 2, 2013

(65) Prior Publication Data
US 2014/0320632 A1 Oct. 30, 2014

(30) Foreign Application Priority Data

Oct. 28, 2011 (DE) .................. 10 2011 117 310
Oct. 26, 2012 (WO) .................. PCT/EP2012/004488

(51) Int. Cl.
*G06K 9/32* (2006.01)
*G06K 9/00* (2006.01)
(Continued)

(52) U.S. Cl.
CPC ......... *G06K 9/3216* (2013.01); *G01F 23/292* (2013.01); *G01N 35/1016* (2013.01); *G06T 7/0012* (2013.01); *G01N 2035/1025* (2013.01)

(58) Field of Classification Search
CPC ... G06K 9/3216; G06T 7/0012; G01F 23/292; G01N 35/1016
(Continued)

(56) References Cited

U.S. PATENT DOCUMENTS 6,388,750 B1 * 5/2002 Liu ....................... G01F 23/292
356/246
2004/0231438 A1 * 11/2004 Schwartz .............. B01L 3/0217
73/864.17
(Continued)

OTHER PUBLICATIONS

Clavius ("Photography Crosshairs," pub. Mar. 2010, available at http://www.clavius.org/photoret.html).*
(Continued)

*Primary Examiner* — Sath V Perungavoor
*Assistant Examiner* — Patricia I Young (57) ABSTRACT

The present invention relates to a device useful for inspecting a sample. The device includes a camera in order to arrange that camera in an image field so that an interface line and a marker of the camera can be imaged as a recorded image. The device also has an evaluation unit which allows an evaluation of the recorded image and the marking in order to provide information to the observer.

37 Claims, 4 Drawing Sheets

(51) Int. Cl.
    *G06F 19/00*     (2011.01)
    *G01N 1/14*      (2006.01)
    *G01N 21/59*     (2006.01)
    *G01F 23/292*    (2006.01)
    *G01N 35/10*     (2006.01)
    *G06T 7/00*      (2017.01)

(58) Field of Classification Search
    USPC ........................................................ 348/86
    See application file for complete search history.

(56) References Cited

U.S. PATENT DOCUMENTS

2007/0021929 A1* 1/2007 Lemmo ............ G01N 35/00613
                                                702/22
2007/0177778 A1* 8/2007 Massaro ............ G01N 35/1016
                                                382/128

OTHER PUBLICATIONS

Li ("An Introduction to Focus Stacking," Digital Photography School, pub. Jul. 2010, available at http://digital-photography-school.com/an-introduction-to-focus-stacking/).*

* cited by examiner

DEVICE AND METHOD FOR INSPECTING A VOLUME OF A SAMPLE

This application is a National Stage Application of PCT/EP2012/004524 filed Oct. 29, 2012, which claims priority from PCT Application No. PCT/EP2012/004488 filed on Oct. 26, 2012 and German Application No. DE 10 2011 117 310.6 filed on Oct. 28, 2011. Each of these applications is hereby incorporated by reference herein in its entirety.

BACKGROUND OF THE INVENTION

The invention relates to a device and a method for inspecting a volume and/or the composition of a sample, in which an interface is formed in a pipette between the sample and a first fluid which is adjacent to the sample, said interface being optically perceptible outside the pipette as an interface line between the sample and the first fluid that extends essentially horizontally. The invention further relates to the use of a camera with a marking in an image field of the camera to carry out such a method.

In DE 10 2008 022 835 B3, a device is described as an analyser for analysing biological or chemical samples using a reagent liquid added via a pipette. A work plate is arranged so that it can be horizontally pivoted on a base plate to retain the samples in a sample holder, for example, a microtitre plate, which features several cells to retain the samples. The cells are also called slots, cavities or wells, occasionally also droplets. Arranged above the work plate is a robot manipulator, which has a horizontal support arm with a slide, said slide having a needle system attached that moves in a vertical direction. The needle system comprises several hollow needles as pipettes, which come to a stop at the same time over a single well, whereby one of the hollow needles pours the reagent liquid into the well. After a reaction or incubation time the solution, which is made of the sample in the well and the added reagent liquid, is suctioned off by a second hollow needle, supplied with a washing solution by a third hollow needle, and then suctioned off again by the second hollow needle. Using the three hollow needles, a single well is therefore supplied with reagent liquid and washing solution. The analyser itself does not contain any elements for evaluating the sample or solution in the well, said sample or solution is evaluated at a later stage by an expert. The wells with the samples or solutions feature barcodes to identify them, with the analyser featuring a device to read these barcodes in its rear section. When reacting with the reagent liquid the samples undergo a colour change and/or a fluorescence, which can be analysed and/or evaluated using a photometer for measuring colour.

As a result of the great number of solutions that are to be produced from a sample and a reagent liquid, which need to be produced as part of complete test series, it is necessary to produce these solutions under stable process conditions at high process speed and by using as low quantities as possible for the sample and the reagent liquid. In addition, the wells should be loaded in as simple a manner as possible for cost reasons. The analyser described above is disadvantageous inasmuch as the needle system with three needles as pipettes only adds a reagent liquid to a well in the amount to be pipetted and the amount that is to be pipetted is set via a drive associated with the first needle, which only guarantees the required process accuracy in terms of the quantity being set to a limited extent.

SUMMARY OF THE INVENTION

The object of the invention is therefore to avoid the disadvantages of the prior art, by producing a solution from a sample and a fluid, for example in the form of a reagent or dilution liquid, using the lowest possible quantities for the sample and the fluid at high process speed.

This object is achieved by means of a device according to claim 1, a method according to claim 8 and using a camera according to claim 13. Advantageous further embodiments of the invention are the subject of dependent claims.

A device according to the invention for inspecting a volume and/or the composition of a sample comprises a pipette, in which an interface is formed between the sample and a first fluid which is adjacent to the sample, said interface being optically perceptible outside the pipette as an interface line between the sample and the first fluid that extends essentially horizontally. The device further comprises a camera with a marking, which is arranged in an image field of the camera, such that the interface line and the marking can be reproduced in a recorded image. Lastly, the device comprises an evaluation unit, which can be used to evaluate whether the marking is at the same height as the interface line in the recorded image. By using a camera with a marking in the image field of the camera, the position of the interface line relative to the pipette, for example to a tip of the pipette or to another reference point related to the pipette, and thereby the volume of the sample within the pipette can be accurately determined. As the interface line is reproduced on an image recorded using the camera in addition to the marking, it can be evaluated, for example, by comparing the recorded image with one or more reference images, whether the marking is at the same height as the interface line. The marking, which is only in the image field of the camera, may be formed in addition to other embodiments as an inspection line, inspection point, inspection spot or inspection cross that extends essentially horizontally and which is at the same height as the interface line if the interface line is aligned with the inspection line. A comparison where required of the recorded image with a reference image for evaluation can be made, for example, by comparing the brightness levels of different pixels of the recorded image with the brightness levels of different pixels of the reference image, which are located at relevant positions on the recorded image and the reference image and if the brightness levels are consistent in a specified range of values, a conformity of the brightness levels is determined. This pattern matching between the recorded image and the reference image can take place automatically using a PC (personal computer). In the event that the sample displays a high contrast to the first fluid and the interface line is reproduced at high quality in the recorded image, a comparison of this image with a reference image can be omitted and evaluation can take place based on a pre-defined selection criterion.

According to the invention, the pipette is calibrated such that when placing the marking at the same height as the interface line, the sample has a pre-defined volume, which is limited by a tip of the pipette as well as by the interface. By calibrating the pipette in the area of the pipette that comprises the pipette tip it is possible to ascertain whether the sample is at the pre-defined volume using just one recorded image. In this way, the sample, which can be a fluid, in particular a liquid, can be set accurately to a specified quantity even when being drawn up into the pipette. As the marking is arranged as an inspection line only in the camera, more specifically in the image field of the camera, a virtual calibration mark may be referred to as a calibration line when using calibrated pipettes. As a result of precisely setting the sample quantity even at the stage of drawing up/ejecting the sample into/out of the pipette, the pipetting process can be inspected inline or online. By using a calibrated pipette and placing the marking at the same height as the interface line, not only is it ensured that a sufficient sample volume is available for the subsequent analysis, but that there is a specified sample volume that permits analysis and this avoids an unnecessarily excessive sample volume, which may be required for other analyses. Blood, serum and/or cellular fluid can be considered for the sample substance. Other substances for the sample, which can be a biological or chemical sample, are possible.

According to the invention it is further provided that the pipette is arranged between a light source and the camera such that a spectrum of light beams of the light source that have passed through the sample can be recorded by the camera. In this case the evaluation unit, which compares the marking in the recorded image with the position of the interface line, comprises additional means which compare the recorded spectrum with a reference spectrum and establish whether, in accordance with the recorded spectrum, the composition of the sample corresponds to that of the reference spectrum.

According to the invention it is further provided that the pipette is arranged between a light source and the camera such that a spectrum of light beams of the light source can be recorded by the camera, said light beams having passed through a meniscus and/or part of the sample directly beneath the meniscus of the sample, which is formed at the edge of the interface to an inner wall of the pipette and acts as a prism-like optical element. According to the invention, the term "directly beneath the meniscus" refers to at least the height of 0.5 times, in particular 1.0 times and preferably 1.5 times the meniscus and as a maximum the height of 3 times, 4 times, in particular 5, 6, 7, 8 times, particularly preferably 10 times the height of the meniscus. In this case the evaluation unit is set up using a comparison of the recorded spectrum with a reference spectrum to evaluate whether the composition of the sample in accordance with the recorded spectrum corresponds to a composition in accordance with the reference spectrum. The meniscus occurs as a curvature of the interface of the sample, as a fluid with liquid property at the edge of the interface of the sample to the first fluid, said edge being adjacent to the inner wall of the pipette. Light beams of a light source arranged outside of the pipette, for example a white light source, pass through the at least partially transparent wall of the pipette, then travel through the meniscus formed by the sample, and are detected by the camera after travelling through the pipette. Here, as a result of its form, the meniscus acts as a prism or prism-like optical element, which is why the light striking the meniscus is split into different light beams according to the light frequency upon travelling through the prism. As the deviation of the incident light beams from their direction of incidence at the outer edges of the meniscus when passing through the meniscus is dependent on the sample-specific refraction index of the sample, which in turn depends on the light frequency, the (chemical) composition of the sample can be deduced on the basis of the spatial brightness distribution, at adequate spatial resolution of the camera, for example an electronic matrix camera, in particular a CCO (Charge Coupled Device) or CMOS (Complementary Metal Oxide Semiconductor) camera. Depending on the arrangement of the light source, the pipette and the camera to each other, both concave and convex menisci of a sample can be used to determine the composition of the sample. In principle, substances dissolved in the sample or undissolved components in the sample, for example impurities, can also be determined in this way. In addition, for inspecting the volume of the sample it can then be ensured that the required quantity of the sample with the required composition of the sample is used which achieves an essential certainty factor when pipetting.

Preferably the evaluation of the composition of the sample is used to establish whether there are haemolytic and/or lipaemic factors in the sample.

In this way, when using serum or plasma, it can be established whether the tests are affected by lipids, haemoglobin or bilirubin. Interferences at elevated quantities (lipids to 20 mg/ml, haemoglobin to 800 µg/ml, bilirubin to 200 µg/ml) may affect the reaction kinetics and distort the results. In the case of samples with lipaemic components the distortion is partly caused by the fats and/or lipids, which may contain cholesterol-rich components, swimming on the surface of the sample, being suctioned off using the pipette for the volume determination instead of the serum or the plasma. This may then result in a volume distortion of the sample being determined and consequently interfere with or distort the analysis result. For these reasons, according to the invention the composition of a sample is preferably performed at the surface as the fat and/or lipid-containing layers preferably separate at the surface. The composition of the sample is therefore preferably measured in the area of the upper interface line of the sample. According to the invention it is equally possible to perform a turbidimetric measurement straight through the sample. It is also possible according to the invention to combine or carry out successively both measurement methods for determining the composition of a sample to achieve increased inspection reliability. In contrast to the interference and/or distortion of the measurement as a result of high-fat components of a sample, haemolytic components if these are present in a sample, interfere with or influence the measurement firstly as a result of their red or brown colours and secondly by the fact that certain reactions are inhibited by haemolytic components. According to the invention it is therefore advisable to determine the composition of a sample before or alongside inspecting the volume.

According to the invention it is also possible to establish flocculation of the sample using one and/or both measurement methods for determining a composition of a sample.

By more precisely inspecting the volume and the composition of a sample, a greater degree of inspection reliability is achieved, which in turn enables false-positive or false-negative samples to be more dependably excluded.

Furthermore the evaluation can establish whether plasma is suitable for transfusions or has to be rejected for health reasons. Accordingly, as a result of the inspection not only is process reliability assured but also the production and use of health-compliant substances.

In the preferred embodiment the first fluid which is adjacent to the sample, is formed of a gas bubble, in particular an air bubble, with the gas bubble being arranged in the pipette between the sample and a second fluid which is adjacent to the gas bubble. Arranging the gas bubble between the sample and the second fluid ensures that the sample is arranged so that it is separate from the second fluid so that the sample and the second fluid do not mix. In this way several fluids can be provided for pipetting in just one pipette. Contrary to the teaching which is disclosed in DE 10 2008 022 835 B3, it is no longer necessary to provide a separate needle, which is a pipette, for a fluid that is being pipetted. The second fluid can, for example, be a dilution fluid for diluting the sample or a comparative fluid for comparison with the sample. In principle it is also possible that there is not just one gas bubble for separating the sample from the second fluid in the pipette, but several gas or air bubbles for separating the respective fluids which are adjacent to the air bubbles. In this way in just one pipette, a large number of different fluids can be placed in a process-stable form for pipetting. Using the device according to the invention for volume inspection ensures in particular that in addition to the volume of the sample, the volume of the second fluid can also be accurately inspected or set. Inasmuch as in addition to the marking on a recorded image not only is the interface formed between the first fluid and the gas bubble, but the further interface is formed between the gas bubble and the second fluid, in just one recorded image as a result of the positioning of the marking to the interface line between the sample and the gas bubble and to the further interface line between the gas bubble and the second fluid, both the volume of the sample and the volume of the second fluid can be inspected or set.

If the depth of field of the camera used to record the image or other imaging or image processing characteristics and/or parameters [number of pixels, brightness override, characteristic colour shift at boundary layers (indirect measurement of the surface tension)] are not adequate to form both the interface line between sample and gas bubble and the further interface line between gas bubble and second fluid at an optical quality on the recorded image that is adequate for evaluation, the image can be composed of two partial images. The first partial image then forms the section of the pipette from its tip to the interface line between the sample and gas bubble. The second partial image forms the section of the pipette with the further interface line between the gas bubble and the second fluid. The outer edges of both partial images border each other between the interface line and the further interface line, i.e. in the gas bubble, so that a complete image results from the section of the pipette with the sample, the gas bubble and the second fluid, in that the outer edges of the pipette align at the transition between both partial images. By aligning both partial images to each other, the further interface line reproduced in the second partial picture can be applied to the tip of the pipette reproduced in the first partial image. This alignment is made easier if the outer edges of both partial images overlap in the area of the gas bubble because the partial images can be aligned so that in the area of the overlap, the outer edges of the pipette lie on top of each other. In the case of overlapping partial images, the image information itself is used instead of the outer edges of the partial images for aligning the partial images to each other.

As a result of the conical form of the pipette in the area of the pipette tip it is also possible alternatively or additionally to the combined partial images, to align the pipette to the lens of the camera so that the ends of the interface line and the further interface line facing the lens display the same or similar distance to the lens. In this case it is not the longitudinal axis of the pipette but the outer edge of the pipette facing the lens that is essentially vertical to the optical axis of the lens or of the camera, and the ends of the interface line and the further interface line facing the lens display the same or similar distance to a point of intersection of the optical axis with the outer edge of the pipette that is facing the lens. The longitudinal axis of the pipette can be rotated to the optical axis by half a cone angle in that the pipette is rotated to the lens or the lens to the pipette, for example by using a computerised electric motor. A recorded image composed of partial images and/or a rotation of the longitudinal axis of the pipette to the optical axis by half a cone angle is not only possible when recording an image of an interface line between a sample and a first fluid in a pipette, but also when recording an image of a first section of a first pipette and a second section of a second pipette. Reference is made at this point to the disclosure in the parallel German patent application made by the applicant of this application with the file number DE 10 2011 117 323.8 and internal file number AES 80207, to the description pages 8 to 11, 17, 22-27 and FIG. 4, in which a recorded image composed of partial images and/or a rotation of the longitudinal axis of the pipette to the optical axis by half a cone angle of two pipettes is described and which is included as a disclosure in the present application by reference.

The volume of the sample, the first fluid and/or the second fluid can be set by shifting the interface line between the sample and first fluid or the interface line between the first fluid and second fluid as a result of moving the sample, the first fluid and/or the second fluid relative to the pipette. This setting of the volume of the sample can take place while a sample, the first fluid and/or the second fluid is being drawn up or ejected, which reduces the process time for pipetting instead of performing this setting once the sample, the first fluid and/or the second fluid has been drawn up into a pipette or ejected out of a pipette.

According to the invention an analyser is provided, for example the analyser described in DE 10 2008 022 835 B3, for analysing biological or chemical samples using a reagent liquid added via a pipette provided with the device according to the invention. As a result of the additional inspection of the volumes of the sample, the first and/or second fluid, if applicable supplemented by an inspection of the composition of these fluids, increased process reliability and process speed at a high level of automation can be achieved.

The method according to the invention for inspecting a volume of a sample comprises the provision of a pipette, in which an interface is formed between the sample and a first fluid which is adjacent to the sample, said interface being optically perceptible outside of the pipette as an interface line between the sample and the first fluid that extends essentially horizontally, an arrangement of a marking of a camera in an image field of the camera such that the interface line and the marking can be reproduced on a recorded image and an evaluation of whether the marking is the same height as the interface line in the recorded image. The above embodiments of the device according to the invention apply correspondingly to the method according to the invention. In this respect, as already explained, the evaluation preferably takes place while the sample is being drawn up via a tip of the pipette.

A further embodiment of the invention provides for an arrangement in the pipette of the first fluid in the form of a gas bubble, in particular air bubble, between the sample and a second fluid which is adjacent to the gas bubble, and a mixing of the sample, which is present in the form of a sample liquid, with the second fluid to achieve the sample being ejected out of the pipette, the gas bubble being ejected together with the second fluid and the sample and the second fluid being drawn up for mixing in the pipette. In this way, using just one single pipette the sample can be dispensed and the second fluid added and mixed with the sample. This procedure ensures that the sample is completely ejected out of the pipette and the sample is mixed with the second fluid. When inspecting the volume of the mixture, which consists of the sample and second fluid, after drawing up the sample and the second fluid, by evaluating whether in a recorded image the marking is at the same height as an interface line between the mixture of the sample and the second fluid and as an air bubble adjacent to the mixed liquid, it can also be inspected or set, whether the sample and second fluid in mixed form is at the required volume.

Lastly, the invention relates to the use of a camera with a marking in the image field of the camera to carry out the method according to the invention. Any camera of sufficient quality may be used for this purpose. Quality parameters are, in particular, the resolution of the camera, its focal distance, aperture, field of depth and sensitivity to light.

The device according to the invention and/or the analyser according to the invention and/or the method according to the invention can be used to record one or more wells, for example of a microtitre plate in a further image and to evaluate the further recorded image information, for example, one or more colour changes of one or more samples in one or more wells. The image can be recorded according to the invention by turning away or moving away the camera after recording the recorded image of the interface line between the sample and the first fluid which are arranged in the pipette, for example by essentially 90 degrees in the direction of the well or wells. Following the recording of the recorded image the camera can therefore be rotated or pivoted for recording another image such that on the further image one or more wells in which the sample is arranged, can be reproduced. In one embodiment the camera is directed vertically at the pipette for recording the image of the pipette and after recording this image it is directed horizontally at one or more wells arranged beneath the camera. Corresponding devices and methods for recording the image and evaluating a recorded image of one or more wells or one or more samples, which are retained in one or more wells, for which the device according to the invention and/or the analyser according to the invention and/or the method according to the invention can be used, are described in the parallel German patent applications of the applicant of the present application with the file reference DE 10 2011 117 311.4 with the internal file reference AES 80205 and DE 10 2011 117 320.3 with the internal file reference AES 80206, which are included as a disclosure in the present application by reference in each case.

Further exemplary embodiments and advantages of the invention are explained in the following on the basis of the figures. For greater clarity, the figures are not shown true to scale or proportion with the exception of FIG. 1. Unless specified otherwise, in the figures the same references refer to the same parts with the same meaning.

BRIEF DESCRIPTION OF THE FIGURES

FIG. 5 shows the arrangement illustrated in FIG. 2 in an enlarged presentation, FIG. 6 schematically shows a recorded image of a filled pipette, which is composed of two partial images, and a camera rotated by half a cone angle vertically along the longitudinal axis of a pipette.

DETAILED DESCRIPTION OF THE INVENTION

Figure 1:
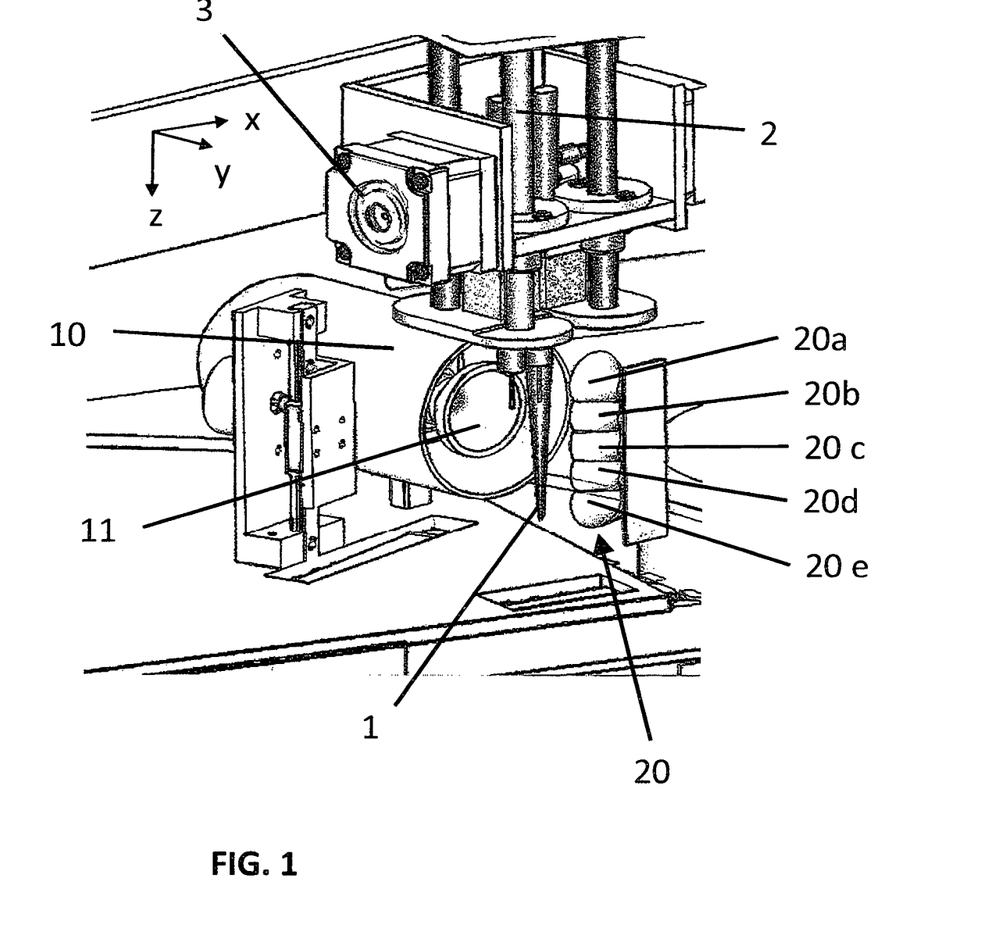
FIG. 1 shows a three-dimensional, proportional representation of an optical arrangement of a pipette, a camera and a light source in accordance with a first embodiment of the invention.

FIG. 1 shows an optical arrangement in which a pipette 1, whose longitudinal axis is aligned in a z direction, is arranged between a camera 10 aligned in a y direction and a light source 20. The pipette 1 is attached to a pipette holder 2 of a robot manipulator (not shown), with the pipette holder 2 being adjustable in the z direction using a motor 3, by means of which the pipette 1 can also be moved in the z direction. The camera 10, for example a CCD camera, features a lens 11 and an image field, which is adequate to record as an image at least part of a section of the pipette 1, which does not extend over the entire width of the pipette in an x direction. Preferably, using the camera 10 a section of the pipette 1 can be recorded as an image over the entire width of the pipette in an x direction. The light source 20 comprises several partial light sources 20a to 20e, which can be attached to a joint carrier as shown in FIG. 1. As a light source, for example, a conventional light bulb, an LED (Light Emitting Device), a gas discharge lamp, a laser or other light sources are considered, which at least partially cover the visible frequency spectrum. Other frequency ranges of the light radiated from the light source 20 are possible. Both point light or quasi-point light sources are possible, for example the partial light sources 20a to 20e, or also surface lights as light source 20, in which preferably full illumination is given over the extension of pipette 1 in the z direction from the tip of pipette 1 to the pipette holder 2. The pipette 1 is at least partially transparent for the light generated by the light source 20, with the light transmitted through the pipette striking the lens 11 of the camera 10 and being detected by said camera. Using the pipette holder 2, empty pipettes, such as pipette 1, can be incorporated from an empty pipette store (not shown), moved in the x direction and lowered in the z direction, to draw up a sample in the form of a fluid out of a well of a sample carrier, for example a microtitre plate, which is arranged in the xy-plane beneath the camera 10 (not shown).

Figure 2:
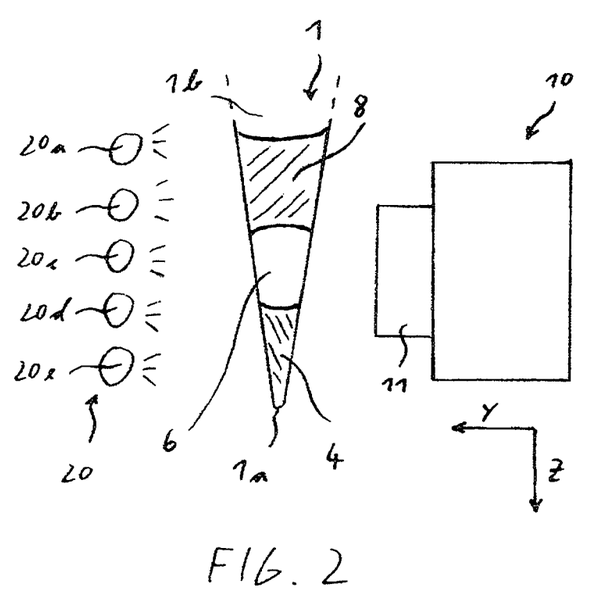
FIG. 2 shows a schematic diagram of the arrangement shown in FIG. 1 in a lateral view.

FIG. 2 shows the optical arrangement illustrated in FIG. 1 of a pipette 1, a camera 10 and a light source 20 schematically illustrated, in which the pipette 1, which features a pipette tip 1a in the z direction and an opening 1b opposite to the z direction as a result of its conical form, is filled with a sample 4, a first fluid 6 and a second fluid 8. The sample 4 is a fluid, in particular a liquid, for example in the form of blood, serum and/or cellular fluid. The first fluid 6 can be a liquid, which should not be mixable as far as possible with the sample 4, or a gas, in particular air, in which an interface is formed between the sample and the first fluid, said interface being optically perceptible outside the pipette 1 as an interface line between the sample and the first fluid that extends essentially horizontally. Above the first fluid, a second fluid 8 is arranged in the pipette 1 in a direction opposite to the z direction, in which the composition of the second fluid may correspond or differ to the composition of sample 4. The second fluid can, for example, be a dilution fluid for diluting the sample 4 or a comparative fluid for comparison with the sample 4. When forming the first fluid as a gas or air bubble here, mixing of the sample with the second fluid is avoided by means of the gas or air bubble being arranged as a separation buffer between the sample and the second fluid. In this way several fluids can be drawn up in just one pipette 1 which is provided for pipetting. When introducing several gas or air bubbles into pipette 1, more than two fluids can be placed in the pipette 1 so that they do not mix. The pipette 1 is arranged between the light source 20 and the camera 10 in a transmitted light arrangement in which the light passes through the pipette, the sample and/or the first fluid and/or the second fluid and is detected by the camera 10. Alternatively or additionally it is also possible to arrange the light source 20 towards the pipette 1 on the same side as the camera 10. In this case the pipette is radiated in the y direction by the light source 20 and the light reflected by the pipette 1, the sample 4 and/or the first fluid 6 and/or the second fluid 8 is detected by the camera 10.

FIG. 3 shows three stages of filling the pipette 1 with the sample 4, a first fluid 6, which is adjacent to the sample 4, and a second fluid 8, which is adjacent to the first fluid.

Figure 3A:
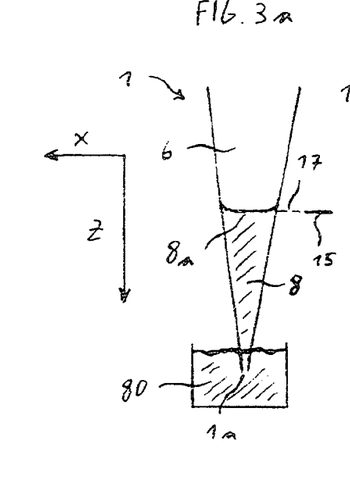
FIG. 3 shows a schematic diagram of the different filling stages of a pipette, in which a gas bubble is arranged between a sample and a fluid.

FIG. 3a shows the pipette 1 lowered in the z direction into a reservoir 80 with a liquid of the second fluid. By means of a (not shown) pump device, which is attached to the pipette holder 2 or is incorporated in said pipette holder, the second fluid 8 in the pipette 1 is drawn up in the direction opposite to the z direction. Above the second fluid 8 in the direction opposite to the z direction, the fluid 8 is adjacent to an air bubble 6, which therefore results in the pipette 1 being an empty pipette filled with air before the pipette 1 is filled with the second fluid 8. At the air bubble 6 an interface is formed with the second fluid, said interface being optically perceptible outside the pipette as an interface line 8a between the second fluid and the air bubble 6 that extends essentially horizontally. During the drawing up of the second fluid 8, an image of the pipette 1 is recorded using the camera 10 such that a marking 15 of the camera arranged in the image field of the camera 10 is reproduced on the recorded image together with the interface line 8a. During the drawing up of the second fluid 8 an evaluation unit continuously evaluates whether the marking 15 is at the same height as the interface line 8a in the images recorded by the camera 10, which can be in the form of a video. In the forming of the interface line 8a as a concave meniscus as a result of a curvature of the outer areas of the interface line 8a in the direction opposite to the z direction, an underside 17 of the concave meniscus can be used to determine whether the marking 15 (in the z direction) is at the same height as the interface line 8a. Provided that the measurements of the pipette 1 and the position of the pipette tip in the z direction are defined, a pre-defined volume of the second fluid 8 can be calculated, which is limited by the tip 1a of the pipette 1 in addition to the interface 8a. Provided that the marking 15, which is shown in FIG. 3a as an inspection line, is then at the same height as the interface line 8a, when using a pipette 1 calibrated in this way, the pre-determined calculated volume of the second fluid is drawn up in the pipette 1. As an alternative to a calculation, the pipette 1 can also be calibrated empirically by determining the volumes of the second fluid depending on the fill level of the second fluid 8, i.e. the height of the interface line 8a in the z direction.

Figure 3B:
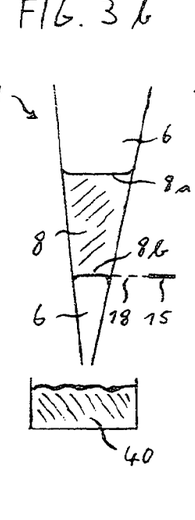
Figure 3C:
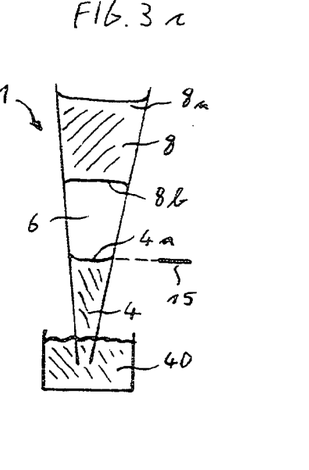

FIG. 3b shows the pipette 1 being pulled out of the reservoir 80 in the direction opposite to the z direction, in which by moving the second fluid 8 in the direction opposite to the z direction, an air bubble 6 is formed beneath the second fluid 8 in the z direction. As it is provided that beneath the second fluid 8, a sample 4 should be arranged in the z direction in the pipette 1, which should be separated via the air bubble 6 from the second fluid, a minimum volume is provided for the air bubble 6, which ensures that the sample 4 and the second fluid 8 do not mix. For this reason a further image is recorded using the camera 10 to evaluate whether the marking 15 in the z direction is at the same height as the interface line 8b, which is formed between the second fluid 8 and the air bubble 6 beneath the second fluid 8 in the z direction. As the interface line 8b is formed as a convex meniscus, the upper side 18 is used instead of the underside 17 in FIG. 3a to evaluate whether the marking 15 is at the same height as the interface line 8b. In addition to inspecting the volume of the second fluid 8 the evaluation of the interface line 8b between the second fluid and the air bubble 6 is also used to inspect the volume of the air bubble 6. When the required volume for the air bubble 6 is achieved the pipette 1 can be lowered in the z direction into a reservoir 40 with sample liquid. This position of the pipette 1 is shown in FIG. 3c. By raising the second fluid 8 in the direction opposite to the z direction using the pump device, also called the drive, sample liquid is drawn up into the pipette 1 such that an interface is formed between the sample 4 which is created by the sample liquid that is drawn up, and the air bubble 6, said interface being optically perceptible outside of the pipette as interface line 4a. As soon as this interface line 4a is at the same height as the marking 15, which can be established by an evaluation unit by means of comparing a recorded image with a reference image, the sample 4 and the second fluid 8 are no longer moved by the pump device relative to the pipette 1 and the pipette 1 is pulled out of the reservoir 40 in the direction opposite to the z direction. In this way, the volume of the sample 4 in the pipette 1, the volume of the air bubble 6 and the volume of the second fluid 8 are at the pre-defined values.

Figure 4:
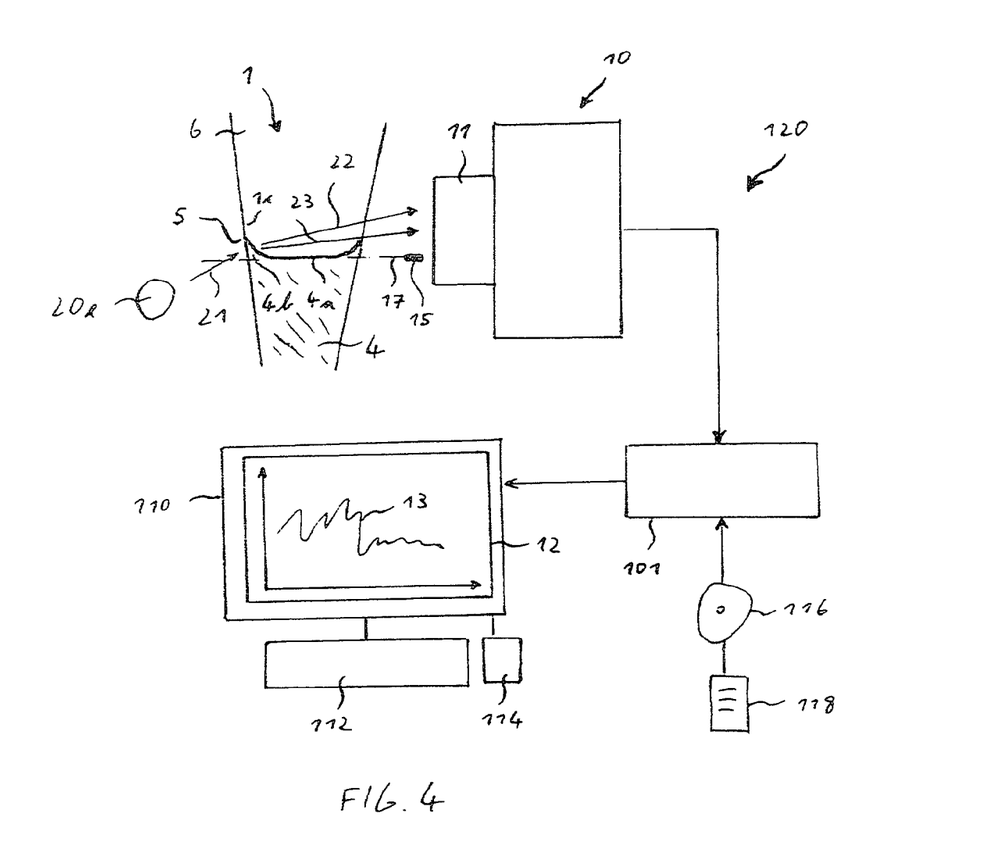
FIG. 4 shows a schematic diagram of the device according to the invention with pipette, camera and evaluation unit for evaluating a meniscus of the sample, which is formed at one edge of an interface of the sample to an inner wall of the pipette.

FIG. 4 shows the device 120 according to the invention for inspecting the volume of the sample 4, in which a light source 20e, which may be formed of an essentially point light source, emits a light beam 21 in the direction of the pipette 1, which passes through a meniscus 4b of the sample 4, which is formed at one edge 5 of the interface to an inner wall 1e of the pipette 1. The meniscus 4b is formed as a concave meniscus as a result of the curvature of the interface of sample 4 to the first fluid 6. The meniscus 4b acts as a prism or as a prism-like optical element such that the light beam 21 entering the meniscus 4b is deflected or broken upon exiting the meniscus 4b into light beams 22, 23, which, depending on their frequency, strike the lens 11 of the camera 10 at a different angle to the direction of incidence of light beam 21. Consequently, light beam 22, for example, at a line of the underside 17 of the meniscus 4b which corresponds to the optical axis of lens 11, features a greater angle than light beam 23. By evaluating the spatial resolution of the brightness distribution in an image 12 recorded by the camera 10, the spectrum 13 of the sample 4 creating the meniscus 4b can be determined. As the refraction index of sample 4 then depends on the frequency of the light of the light source 20e entering the meniscus 4b of sample 4, meniscus 4b which acts as a prism-like optical element, generates a spectrum that is characteristic of the particular chemical composition of the sample 4. By comparing the recorded spectrum 13 with a reference spectrum, the evaluation unit 101 can determine whether the composition of the sample 4 in accordance with the recorded spectrum 13, corresponds to a composition in accordance with the reference spectrum. It can then be determined by means of determining the spectrum of sample 4, whether haemolytic and/or lipaemic factors are present in the sample 4. These factors result from an unclean work up, for example of a serum and are detrimental to the function of the sample or the analysis of the sample and therefore undesired. It can therefore be established using the spectrum of the sample 4 whether the sample 4 can be utilised. The result of the applicability of the sample 4 can be given or expressed immediately after determining the spectrum and/or upon the availability of the analysis results relating to sample 4. For this purpose the evaluation unit 101, which can be designed in the form of software and/or hardware on a computer or PC, is connected to a monitor 110 on which the recorded image 12 of the camera 10 can be presented. The evaluation unit 101 can be operated using a keyboard 112 and/or a mouse 114. By using suitable executable software or a computer program 116 on the computer being used as the evaluation unit 101, said software or computer program may be stored for example on a CD, a DVD or a memory stick 118 as a data storage device, the volumes determined using the marking 15 of the sample 4 and/or the first and second fluids 6, 8 located in the pipette 1 and/or the compositions of sample 4, the first fluid 6 and the second fluid 8, can be determined by evaluating the images recorded by the camera 10.

Figure 5:
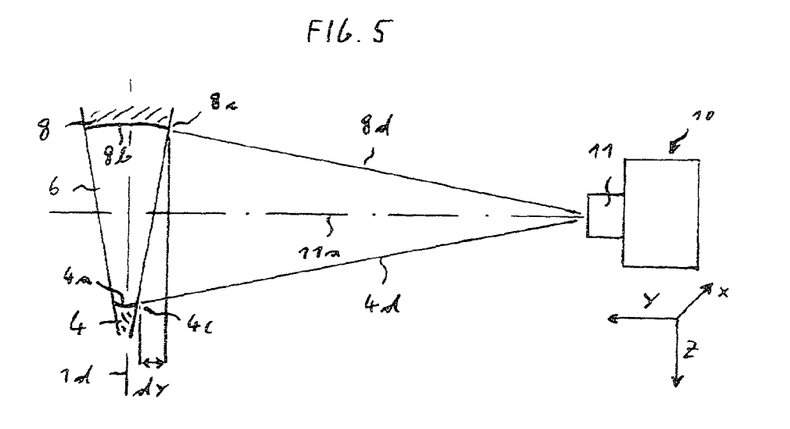

In FIG. 5 the arrangement shown in FIG. 2 of a pipette 1 and camera 10 is shown in an enlarged view. The pipette 1 features a longitudinal axis 1*d* orientated in the z direction and a conical form, in which an optical axis 11*a* of the lens 11 or the camera 10 is aligned in the y direction, i.e. vertical to the longitudinal axis 1*d* of the pipette. The interface line 8*b* between the second fluid 8 and the first fluid 6 in the form of a gas bubble features a point 8*c* facing the lens 11 or the camera 10 at a distance 8*d* to the lens 11. The interface line 4*a* between the sample 4 and the first fluid 6 features a point 4*c* facing the lens 11 or the camera 10 at a distance 4*d* to the lens 11. The distance 4*c* is greater in the y direction by the value dy than the distance 8*d* as a result of the conical form of the pipette 1. The value dy is greater, the further the spacing is in the z direction of the interface line 8*b* between the second fluid 8 and the first fluid 6 and the interface line 4*a* between the sample 4 and the first fluid 6 and the greater the cone angle of the pipette 1.

Figure 6A:
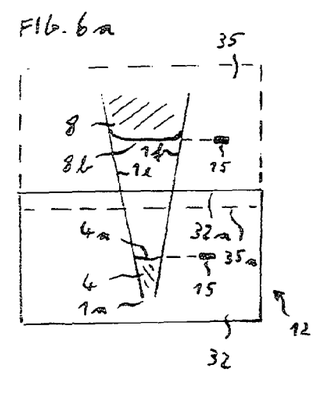

If the field of depth of the camera 10 used for recording the image 12 is smaller than the value dy and is not adequate to reproduce both the interface line 4*a* between the sample 4 and the first fluid 6 and the further interface line 8*b* between the first fluid 6 and the second fluid 8 at an optical quality on the recorded image that is adequate for evaluation, the image 12 can be composed of two partial images 32, 35 as shown as in FIG. 6*a*. The first partial image 32 reproduces the section of the pipette 1 from its tip 1*a* to the interface line 4*a* between the sample 4 and the first fluid 6. The second partial image 35 reproduces the section of the pipette 1 with the further interface line 8*b* between the first fluid 6 and the second fluid 8. Between both interface lines 4*a*, 8*b*, i.e. in the gas bubble of the first fluid 6, the outer edges 32*a*, 35*a* of both partial images 32, 35 can adjoin each other so that a complete image is produced of the section of the pipette 1 with the sample 4, the first fluid 6 and the second fluid 8, in which the outer edges 1*e*, 1*f* of the pipette 1 align at the transition between the two partial images 32, 35. By aligning both partial images 32, 35 to each other, the further interface line 8*b* reproduced in the second partial picture 35 can be applied to the tip 1*a* of the pipette 1 reproduced in the first partial image 32. This alignment is made easier if the outer edges 32*a*, 35*a* of both partial images 32, 35 overlap in the area of the gas bubble of the first fluid 6, because the partial images 32, 35 can be aligned so that in the area of the overlap, i.e. between the outer edge 32*a* of the first partial image 32 and the outer edge 35*a* of the second partial image 35, the outer edges 1*e*, 1*f* of the pipette 1 lie on top of one another as shown in FIG. 6*a*. In the case of overlapping partial images 32, 35, the image information itself is used instead of the outer edges 32*a*, 35*a* of the partial images 32, 35 to evaluate the partial images 32, 35 together. As the first partial image 32 is in an xz plane with the point 4*c* of the interface line 4*a* between sample 4 and the first fluid 6 and the second partial image 35 is in an xz plane with the point 8*c* of the interface line 8*b* between the first fluid 6 and second fluid 8, both partial images 32, 35, can be recorded in a suitable quality for evaluation, independent or virtually independent of the depth of field of the camera 10.

Figure 6B:
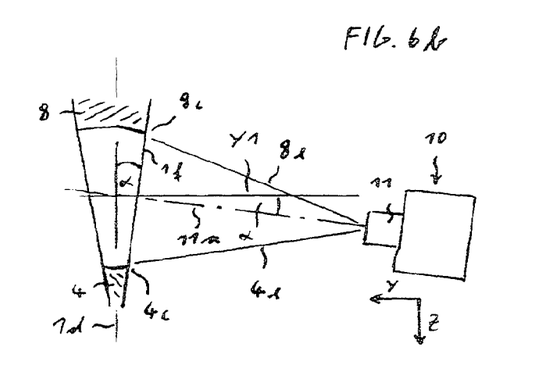

A recorded image 12 that is suitable for the evaluation at a low depth of field of the camera 10, can be obtained alternatively or additionally to the combined partial images 32, 35, if the pipette 1 is aligned to the lens 11 of the camera 10 in such a way that the points 4*c*, 8*c* facing the lens 11 of the interface lines 4*a*, 8*b* between sample 4, the first fluid 6 and second fluid 8 feature the same or similar distances 4*e*, 8*e* to the lens 10 as is shown in FIG. 6*b*. In this case, it is not the longitudinal axis 1*d* of the pipette 1, but the outer edge 1*f* of the pipette 1 that is facing the lens 11, which is essentially vertical to the optical axis 11*a* of the lens 11 or the camera 10, with the points 4*c*, 8*c* that are facing the lens 11, of the interface lines 4*a*, 8*b* between sample 4, the first fluid 6 and second fluid 8 displaying the same or similar distances to a point of intersection of the optical axis 11*a* with the outer edge 1*f* of the pipette 1 which is facing the lens. A perpendicular Y1 can be rotated along the longitudinal axis 1*d* of the pipette 1 to the optical axis 11*a* by half a cone angle α by rotating the pipette 1 towards the lens 11 or, as shown in FIG. 6*b*, rotating the lens 11 towards the pipette 1, for example by using a computerised electric motor. The rotation shown in FIG. 6*b* of the lens 11 by half a cone angle α has the advantage that the interface lines 4*a*, 8*b* in the pipette 1 do not move as a result of rotating the pipette 1, whereby the interface lines on the recorded image 12 are reproduced at a potentially higher quality, for example in the case of samples 4 and/or fluids 6, 8 higher viscosity, than in the case of a rotated pipette 1.

FIG. 7 shows three stages of the pipette 1, which are undertaken to use a pipette to dispense the sample 4, add a second fluid 8 to the sample 4 and to mix the sample 4 with a second fluid 8.

Figure 7A:
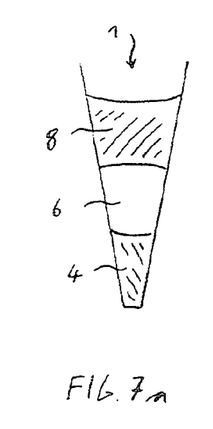
FIG. 7 shows a method according to the invention in which a pipette is used to dispense a sample, add a fluid to the sample and mix the sample with the fluid.
Figure 7B:
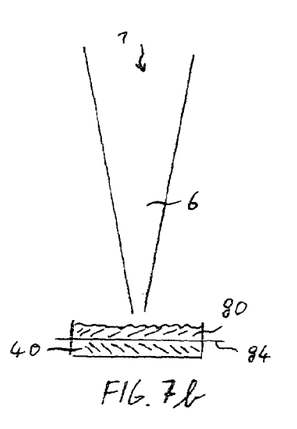
Figure 7C:
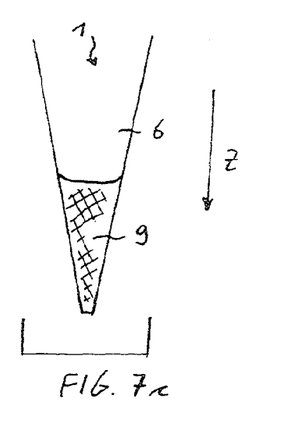

In FIG. 7*a* the sample 4 is a sample liquid, the first fluid 6 a gas or air bubble and the second fluid 8 a liquid. The gas or air bubble is arranged here between the sample liquid of sample 4 and the liquid of the second fluid 8. In a reservoir (not shown), the sample liquid of sample 4 and the liquid of the second fluid 8 are then added one after the other, forming a boundary layer 84 between the reservoir 40 of the sample liquid and the reservoir 80 of the liquid. The non-existent or incomplete mixing of the sample liquid of the sample 4 and the liquid of the second fluid 80 can have various causes, for example the viscosities of the sample 4 and/or of the second fluid 8 may be different or too high. After ejecting the sample 4 and the second fluid 8, the pipette 1 only contains air or another gas in accordance with the process environment as shown in FIG. 7*b*. For the mixing of the sample 4 with the second fluid, the invention provides for the reservoir 40 of the sample liquid of the sample 4 and the reservoir 80 of the liquid of the second fluid 8 to be sucked up into the pipette 1. For this purpose the pipette is moved in the z direction, for example into a well of a microtitre place with the reservoir 40 of the sample liquid and the reservoir 80 of the liquid, and subsequently both reservoirs 40, 80 are suctioned off out of the well (not shown) in the direction opposite to the z direction. As shown in FIG. 7c, both the sample 4 and the second fluid 8 are then drawn up into the pipette 1 as a liquid mixture 9. The mixture does not or does not exclusively take place when the sample 4 and the second liquid 8 are ejected, but occurs first as a result of the sample 4 and the second fluid 8 being drawn up into the pipette 1. The liquid mixture 9 is released after being drawn up into the pipette 1 into the same well in which the sample 4 and the second fluid 8 were previously released, or it is released into another well. If the necessary level of mixing is not achieved, once the liquid mixture 9 has been ejected into the well, the liquid mixture 9 can be taken up into the pipette 1 for a second time. The release and take up of the liquid mixture 9 can be repeated several times and in principle any number of times until the required level of mixing is achieved.

What is claimed:

1. A device (120) for inspecting a volume and a composition of a sample (4), said device comprising:
   (a) a pipette (1), in which an interface is formed between the sample (4) and a first fluid (6) which is adjacent to the sample (4), said interface being optically perceptible outside the pipette (1) as an interface line (4a) between the sample (4) and the first fluid (6) that extends about horizontally;
   (b) a camera (10) with a marking (15), which is arranged in an image field of the camera (10), such that the interface line (4a) and the marking (15) can be reproduced in a recorded image (12), with the pipette (1) being arranged between a light source (20, 20a-20e) and the camera (10), such that a spectrum (13) of light beams (22-24) of the light source (20, 20a-20e) that have passed through the sample (4) can be recorded by the camera (10); and
   (c) an evaluation unit (101) such as a computer or PC, which compares the marking (15) in the recorded image (12) with a position of the interface line (4a) and in which the evaluation unit (101) comprises additional means which compare a recorded spectrum (13) with a reference spectrum and determine whether the composition of the sample (4) in accordance with the recorded spectrum (13) corresponds to that of the reference spectrum.

2. The device (120) according to claim 1, in which the pipette (1) is calibrated such that when the marking (15) is placed at the same height as the interface line (4a), the sample (4) has a pre-defined volume, which is limited in addition to the interface by a tip (1a) of the pipette (1).

3. The device (120) according to claim 1, in which the pipette (1) is arranged between a light source (20, 20a-20e) and the camera (10) such that a spectrum (13) of light beams (22-24) of the light source (20, 20a-20e) can be recorded by the camera (10), said light beams having passed through a meniscus (4b) and part of the sample directly beneath the meniscus of the sample (4), which is formed at one edge (5) of the interface to an inner wall (1c) of the pipette (1), and the evaluation unit (101) comprises additional means such as software or hardware which compare the recorded spectrum (13) with a reference spectrum and determine whether, in accordance with the recorded spectrum (13), the composition of the sample (4) corresponds to that of the reference spectrum.

4. The device (120) according to claim 2, in which the pipette (1) is arranged between a light source (20, 20a-20e) and the camera (10) such that a spectrum (13) of light beams (22-24) of the light source (20, 20a-20e) can be recorded by the camera (10), said light beams having passed through a meniscus (4b) and part of the sample directly beneath the meniscus of the sample (4), which is formed at one edge (5) of the interface to an inner wall (1c) of the pipette (1), and the evaluation unit such as a computer or PC (101) comprises additional means which compare the recorded spectrum (13) with a reference spectrum and determine whether, in accordance with the recorded spectrum (13), the composition of the sample (4) corresponds to that of the reference spectrum.

5. The device (120) according to claim 1 in which the first fluid (6) is formed as a gas bubble, such as an air bubble, and in the pipette (1) the gas bubble is arranged between the sample (4) and a second fluid (8), which is adjacent to the gas bubble, with a further interface being formed between the first fluid (6) and the second fluid (8), said interface being optically perceptible outside of the pipette (1) as a further interface line (8b) between the first (6) and the second fluid (8) and extending about horizontally.

6. The device (120) according to claim 2 in which the first fluid (6) is formed as a gas bubble, such as an air bubble, and in the pipette (1) the gas bubble is arranged between the sample (4) and a second fluid (8), which is adjacent to the gas bubble, with a further interface being formed between the first fluid (6) and the second fluid (8), said interface being optically perceptible outside of the pipette (1) as a further interface line (8b) between the first (6) and the second fluid (8) and extending about horizontally.

7. The device (120) according to claim 3 in which the first fluid (6) is formed as a gas bubble, such as an air bubble, and in the pipette (1) the gas bubble is arranged between the sample (4) and a second fluid (8), which is adjacent to the gas bubble, with a further interface being formed between the first fluid (6) and the second fluid (8), said interface being optically perceptible outside of the pipette (1) as a further interface line (8b) between the first (6) and the second fluid (8) and extending about horizontally.

8. The device (120) according to claim 4 in which the first fluid (6) is formed as a gas bubble, such as an air bubble, and in the pipette (1) the gas bubble is arranged between the sample (4) and a second fluid (8), which is adjacent to the gas bubble, with a further interface being formed between the first fluid (6) and the second fluid (8), said interface being optically perceptible outside of the pipette (1) as a further interface line (8b) between the first (6) and the second fluid (8) and extending about horizontally.

9. The device (120) according to claim 5 wherein
   (a) either the recorded image (12) is composed of at least two partial images (32, 35), in which the interface line (4a) is reproduced on the first partial image (32) and the further interface line (8b) is reproduced on the second partial image (35); or
   (b) the pipette (1) is conically designed and the camera (10) is rotated by half a cone angle ($\alpha$) towards a perpendicular (Y1) along a longitudinal axis (1d) of the pipette (1).

10. The device (120) according to claim 9, wherein the evaluation unit such as a computer or PC (101) comprises additional means to compare the recorded spectrum (13) with a reference spectrum and determine whether haemolytic and lipaemic factors are present in the sample (4).

11. An analyzer for analyzing biological or chemical samples (4) by means of a reagent liquid added using a pipette with a device (120) according to claim 1.

12. A method for inspecting a volume and/or a composition of a sample (4), comprising:
   (a) provision of a pipette (1), in which an interface is formed between the sample (1) and a first fluid (6)

which is adjacent to the sample (1), said interface being optically perceptible outside the pipette (1) as an about horizontal interface line (4*a*) between the sample (4) and the first fluid (6);
(b) arrangement of a marking (15) of a camera (10) in an image field of the camera (10), such that the interface line (4*a*) and the marking (15) can be reproduced on a recorded image (12), with the pipette (1) being arranged between a light source (20, 20*a*-20*e*) and the camera (10), such that a spectrum (13) of light beams (22-24) of the light source (20, 20*a*-20*e*) that have passed through the sample (4) is recorded by the camera (10);
(c) evaluation of whether the marking (15) in the recorded image (12) is consistent with a position of the interface line (4*a*);
(d) comparison of a recorded spectrum (13) with a reference spectrum; and
(e) determination of whether the composition of the sample (4) in accordance with the recorded spectrum (13) corresponds to that of the reference spectrum.

13. The method according to claim 12, characterized in that by comparing the recorded spectrum (13) with a reference spectrum, it is determined whether haemolytic and lipaemic factors are present in a sample (4).

14. The method according to claim 12, wherein
(a) the pipette (1) is arranged between a light source (20, 20*a*-20*e*) and the camera (10) such that a spectrum (13) of light beams (22-24) of the light source (20, 20*a*-20*e*) is recorded by the camera (10), said light beams having passed through a meniscus (4*b*) and part of the sample directly beneath the meniscus of the sample (4), which is formed at one edge (5) of the interface to an inner wall (1*c*) of the pipette (1);
(b) the recorded spectrum (13) is compared with a reference spectrum, and
(c) it is determined whether the composition of the sample (4) in accordance with the recorded spectrum (13) corresponds to that of the reference spectrum.

15. The method according to claim 14 wherein the evaluation takes place while the sample (4) is being drawn up using a tip (1*a*) of the pipette (1).

16. The method according to claim 14 wherein
(a) the first fluid (6) is arranged in the pipette (1) in the form of a gas bubble, such as an air bubble between the sample (4) and a second fluid (8) which is adjacent to the gas bubble;
(b) the sample (1) in the form of a sample liquid with the second fluid (8) is mixed by
(c) ejecting the sample (4) out of the pipette (1);
(d) ejecting the gas bubble together with the second fluid (8); and
(e) drawing up the sample (4) and the second fluid (8) for mixing in the pipette (1).

17. A device (120) for inspecting a volume or a composition of a sample (4), said device comprising:
(a) a pipette (1), in which an interface is formed between the sample (4) and a first fluid (6) which is adjacent to the sample (4), said interface being optically perceptible outside the pipette (1) as an interface line (4*a*) between the sample (4) and the first fluid (6) that extends about horizontally;
(b) a camera (10) with a marking (15), which is arranged in an image field of the camera (10), such that the interface line (4*a*) and the marking (15) can be reproduced in a recorded image (12), with the pipette (1) being arranged between a light source (20, 20*a*-20*e*) and the camera (10), such that a spectrum (13) of light beams (22-24) of the light source (20, 20*a*-20*e*) that have passed through the sample (4) can be recorded by the camera (10); and
(c) an evaluation unit (101) such as a computer or PC, which compares the marking (15) in the recorded image (12) with a position of the interface line (4*a*) and in which the evaluation unit (101) comprises additional means which compare a recorded spectrum (13) with a reference spectrum and determine whether the composition of the sample (4) in accordance with the recorded spectrum (13) corresponds to that of the reference spectrum.

18. The device (120) according to claim 17, in which the pipette (1) is calibrated such that when the marking (15) is placed at the same height as the interface line (4*a*), the sample (4) has a pre-defined volume, which is limited in addition to the interface by a tip (1*a*) of the pipette (1).

19. The device (120) according to claim 17, in which the pipette (1) is arranged between a light source (20, 20*a*-20*e*) and the camera (10) such that a spectrum (13) of light beams (22-24) of the light source (20, 20*a*-20*e*) can be recorded by the camera (10), said light beams having passed through a meniscus (4*b*) and part of the sample directly beneath meniscus of the sample (4), which is formed at one edge (5) of the interface to an inner wall (1*c*) of the pipette (1), and the evaluation unit (101) comprises additional means such as software or hardware which compare the recorded spectrum (13) with a reference spectrum and determine whether, in accordance with the recorded spectrum (13), the composition of the sample (4) corresponds to that of the reference spectrum.

20. The device (120) according to claim 18, in which the pipette (1) is arranged between a light source (20, 20*a*-20*e*) and the camera (10) such that a spectrum (13) of light beams (22-24) of the light source (20, 20*a*-20*e*) can be recorded by the camera (10), said light beams having passed through a meniscus (4*b*) and part of the sample directly beneath the meniscus of the sample (4), which is formed at one edge (5) of the interface to an inner wall (1*c*) of the pipette (1), and the evaluation unit (101) comprises additional means which compare the recorded spectrum (13) with a reference spectrum and determine whether, in accordance with the recorded spectrum (13), the composition of the sample (4) corresponds to that of the reference spectrum.

21. The device (120) according to claim 17 in which the first fluid (6) is formed as a gas bubble, such as an air bubble, and in the pipette (1) the gas bubble is arranged between the sample (4) and a second fluid (8), which is adjacent to the gas bubble, with a further interface being formed between the first fluid (6) and the second fluid (8), said interface being optically perceptible outside of the pipette (1) as a further interface line (8*b*) between the first (6) and the second fluid (8) and extending about horizontally.

22. The device (120) according to claim 18 in which the first fluid (6) is formed as a gas bubble, such as an air bubble, and in the pipette (1) the gas bubble is arranged between the sample (4) and a second fluid (8), which is adjacent to the gas bubble, with a further interface being formed between the first fluid (6) and the second fluid (8), said interface being optically perceptible outside of the pipette (1) as a further interface line (8*b*) between the first (6) and the second fluid (8) and extending about horizontally.

23. The device (120) according to claim 19 in which the first fluid (6) is formed as a gas bubble, such as an air bubble, and in the pipette (1) the gas bubble is arranged between the sample (4) and a second fluid (8), which is adjacent to the as bubble, with a further interface being formed between the first fluid (6) and the second fluid (8), said interface being optically perceptible outside of the pipette (1) as a further interface line (8*b*) between the first (6) and the second fluid (8) and extending about horizontally.

24. The device (120) according to claim 20 in which the first fluid (6) is formed as a gas bubble, such as an air bubble, and in the pipette (1) the gas bubble is arranged between the sample (4) and a second fluid (8), which is adjacent to the gas bubble, with a further interface being formed between the first fluid (6) and the second fluid (8), said interface being optically perceptible outside of the pipette (1) as a further interface line (8*b*) between the first (6) and the second fluid (8) and extending about horizontally.

25. The device (120) according to claim 21 wherein
    (a) either the recorded image (12) is composed of at least two partial images (32, 35), in which the interface line (4*a*) is reproduced on the first partial image (32) and the further interface line (8*b*) is reproduced on the second partial image (35); or
    (b) the pipette (1) is conically designed and the camera (10) is rotated by half a cone angle ($\alpha$) towards a perpendicular (Y1) along a longitudinal axis (1*d*) of the pipette (1).

26. The device (120) according to claim 25, wherein the evaluation unit (101) comprises additional means to compare the recorded spectrum (13) with a reference spectrum and determine whether haemolytic and/or lipaemic factors are present in the sample (4).

27. An analyzer for analyzing biological or chemical samples (4) by means of a reagent liquid added using a pipette with a device (120) according to claim 17.

28. A method for inspecting a volume and a composition of a sample (4), comprising:
    (a) provision of a pipette (1), in which an interface is formed between the sample (1) and a first fluid (6) which is adjacent to the sample (1), said interface being optically perceptible outside the pipette (1) as an about horizontal interface line (4*a*) between the sample (4) and the first fluid (6);
    (b) arrangement of a marking (15) of a camera (10) in an image field of the camera (10), such that the interface line (4*a*) and the marking (15) can be reproduced on a recorded image (12), with the pipette (1) being arranged between a light source (20, 20*a*-20*e*) and the camera (10), such that a spectrum (13) of light beams (22-24) of the light source (20, 20*a*-20*e*) that have passed through the sample (4) is recorded by the camera (10);
    (c) evaluation of whether the marking (15) in the recorded image (12) is consistent with a position of the interface line (4*a*);
    (d) comparison of the recorded spectrum (13) with a reference spectrum; and
    (e) determination of whether the composition of the sample (4) in accordance with a recorded spectrum (13) corresponds to that of the reference spectrum.

29. The method according to claim 28, characterized in that by comparing the recorded spectrum (13) with a reference spectrum, it is determined whether haemolytic and lipaemic factors are present in a sample (4).

30. The method according to claim 28, wherein
    (a) the pipette (1) is arranged between a light source (20, 20*a*-20*e*) and the camera (10) such that a spectrum (13) of light beams (22-24) of the light source (20, 20*a*-20*e*) is recorded by the camera (10), said light beams having passed through a meniscus (4*b*) and part of the sample directly beneath the meniscus of the sample (4), which is formed at one edge (5) of the interface to an inner wall (1 *c*) of the pipette (1);
    (b) the recorded spectrum (13) is compared with a reference spectrum, and
    (c) it is determined whether the composition of the sample (4) in accordance with the recorded spectrum (13) corresponds to that of the reference spectrum.

31. The method according to claim 30 wherein the evaluation takes place while the sample (4) is being drawn up using a tip (1*a*) of the pipette (1).

32. The method according to claim 30 wherein
    (a) the first fluid (6) is arranged in the pipette (1) in the form of a gas bubble, such as an air bubble between the sample (4) and a second fluid (8) which is adjacent to the gas bubble;
    (b) the sample (1) in the form of a sample liquid with the second fluid (8) is mixed by
    (c) ejecting the sample (4) out of the pipette (1);
    (d) ejecting the gas bubble together with the second fluid (8); and
    (e) drawing up the sample (4) and the second fluid (8) for mixing in the pipette (1).

33. A method for inspecting a volume or a composition of a sample (4), comprising:
    (a) provision of a pipette (1), in which an interface is formed between the sample (1) and a first fluid (6) which is adjacent to the sample (1), said interface being optically perceptible outside the pipette (1) as an about horizontal interface line (4*a*) between the sample (4) and the first fluid (6);
    (b) arrangement of a marking (15) of a camera (10) in an image field of the camera (10), such that the interface line (4*a*) and the marking (15) can be reproduced on a recorded image (12), with the pipette (1) being arranged between a light source (20, 20*a*-20*e*) and the camera (10), such that a spectrum (13) of light beams (22-24) of the light source (20, 20*a*-20*e*) that have passed through the sample (4) is recorded by the camera (10);
    (c) evaluation of whether the marking (15) in the recorded image (12) is consistent with a position of the interface line (4*a*);
    (d) comparison of the recorded spectrum (13) with a reference spectrum; and
    (e) determination of whether the composition of the sample (4) in accordance with a recorded spectrum (13) corresponds to that of the reference spectrum.

34. The method according to claim 28, characterized in that by comparing the recorded spectrum (13) with a reference spectrum, it is determined whether haemolytic or lipaemic factors are present in a sample (4).

35. The method according to claim 28, wherein
    (a) the pipette (1) is arranged between a light source (20, 20*a*-20*e*) and the camera (10) such that a spectrum (13) of light beams (22-24) of the light source (20, 20*a*-20*e*) is recorded by the camera (10), said light beams having passed through a meniscus (4*b*) or part of the sample directly beneath the meniscus of the sample (4), which is formed at one edge (5) of the interface to an inner wall (1*c*) of the pipette (1);
    (b) the recorded spectrum (13) is compared with a reference spectrum, and
    (c) it is determined whether the composition of the sample (4) in accordance with the recorded spectrum (13) corresponds to that of the reference spectrum.

36. The method according to claim 30 wherein the evaluation takes place while the sample (4) is being drawn up using a tip (1*a*) of the pipette (1).

37. The method according to claim 30 wherein
(a) the first fluid (6) is arranged in the pipette (1) in the form of a gas bubble, such as an air bubble between the sample (4) and a second fluid (8) which is adjacent to the gas bubble;
(b) the sample (1) in the form of a sample liquid with the second fluid (8) is mixed by
(c) ejecting the sample (4) out of the pipette (1);
(d) ejecting the gas bubble together with the second fluid (8); and
(e) drawing up the sample (4) and the second fluid (8) for mixing in the pipette (1).

\* \* \* \* \*